United States Patent
Taft

(10) Patent No.: US 9,446,082 B2
(45) Date of Patent: *Sep. 20, 2016

(54) TOPICAL COMPOSITION FOR TREATMENT OF SKIN, HAIR AND/OR NAILS AND METHOD OF USING THE SAME

(71) Applicant: Camilla A Taft, North Haledon, NJ (US)

(72) Inventor: Camilla A Taft, North Haledon, NJ (US)

(73) Assignee: Hummingbird Industries, North Haledon, NJ (US)

( * ) Notice: Subject to any disclaimer, the term of this patent is extended or adjusted under 35 U.S.C. 154(b) by 201 days.

This patent is subject to a terminal disclaimer.

(21) Appl. No.: 14/470,246

(22) Filed: Aug. 27, 2014

(65) Prior Publication Data

US 2015/0064213 A1   Mar. 5, 2015

Related U.S. Application Data

(60) Provisional application No. 61/959,559, filed on Aug. 27, 2013.

(51) Int. Cl.

| | |
|---|---|
| *A61K 36/00* | (2006.01) |
| *A61K 36/03* | (2006.01) |
| *A61K 9/00* | (2006.01) |
| *A61K 47/12* | (2006.01) |
| *A61K 47/26* | (2006.01) |
| *A61K 47/42* | (2006.01) |
| *A61Q 19/08* | (2006.01) |
| *A61K 8/97* | (2006.01) |
| *A61Q 5/00* | (2006.01) |
| *A61Q 19/00* | (2006.01) |

(52) U.S. Cl.
CPC .............. *A61K 36/03* (2013.01); *A61K 8/975* (2013.01); *A61K 9/0014* (2013.01); *A61K 47/12* (2013.01); *A61K 47/26* (2013.01); *A61K 47/42* (2013.01); *A61Q 19/08* (2013.01); *A61Q 5/006* (2013.01); *A61Q 19/002* (2013.01); *A61Q 19/004* (2013.01); *A61Q 19/007* (2013.01)

(58) Field of Classification Search
None
See application file for complete search history.

(56) References Cited

FOREIGN PATENT DOCUMENTS

JP    2000072642 A  *  3/2000
JP    2007236386 A  *  9/2007

OTHER PUBLICATIONS

Shin et al, Antibacterial activity of the lactoperoxidase system combined with edible Laminaria hot-water extract as a source of halide ions. Bioscience, Biotechnology and Biochemistry (2012), vol. 76, No. 2, pp. 404-406.*
Product literature Dermikelp Cream 2011 http://www.africanbotanicals.com/All-Products/c166/p399/Dermikelp-Cream-50ml/product_info.html.
Product Literature Dermikelp Shampoo http://www.africanbotanicals.com/All-Products/c166/p401/Dermikelp-Shampoo/product_info.html.
Product Literature Dermikelp Cream 2015 http://www.iheal.co.za/products.html?page=shop.product_details&flypage=flypage.tpl&product_id=2819&category_id=145.
Product information Ecklon Home p. 2015 http://www.ecklon.net/.
Product information Ecklon General Information p. 2015 http://www.ecklon.net/information.htm.
Ecklon Algae Cleansing Bar Product Information 2015 http://www.ecklon.net/products_1.htm.
Ecklon Marine Exfoliating Scrub Product Information 2015 http://www.ecklon.net/products_2.htm.
Ecklon Marine Exfoliating Body Gel Product Information 2015 http://www.ecklon.net/products_11.htm.
Ecklon Intensive Anti-Cellulite and Slimming Gel Product Information 2015 http://www.ecklon.net/products_6.htm.
Ecklon Advanced Body Lotion Product Information 2015 http://www.ecklon.net/products_7.htm.

* cited by examiner

*Primary Examiner* — Qiuwen Mi
(74) *Attorney, Agent, or Firm* — Irving M. Fishman

(57) ABSTRACT

A topical composition includes an amount of a concentrate derived from *Ecklonia maxima* (sea bamboo) effective for treating the skin, hair and/or nails and a dermatologically acceptable carrier.

21 Claims, No Drawings

TOPICAL COMPOSITION FOR TREATMENT OF SKIN, HAIR AND/OR NAILS AND METHOD OF USING THE SAME

FIELD OF THE INVENTION

The present invention relates to topical compositions, and more particularly, a topical composition for treatment of skin, hair and/or nails and method of using the same.

BACKGROUND OF THE INVENTION

Over time, exposure to certain environmental factors such as, for example, excess sunlight, dry air, pollutants, and abrasives, can adversely affect the skin, hair and/or nails. These effects can lead to conditions that are generally considered visually and physiologically undesirable.

Accordingly, there is a need for a topical composition formulated to treat skin, hair, and/or nails afflicted with a condition in need of treatment. There is also a need for a topical composition with an enhanced shelf-life containing actives that are effective in preventing damage associated with aging and environmental stresses, improve visual appearance and promote healing of the skin, and/or nails. There is a further need for a topical composition that is safe, relatively easy to make and apply to the afflicted skin, hair and/or nails.

SUMMARY OF THE INVENTION

The present invention relates generally to a topical composition formulated to treat skin, hair, and/or nails afflicted with a condition in need of treatment, and a method of using the same. The condition may be the result of aging and/or other damage in the skin, hair and/or nails due to environmental effects or stresses. The present invention is especially suitable for use in skin, hair and/or nails treatment applications. The present invention is specifically formulated to prevent or protect the skin, hair and/or nails against such conditions, improve visual appearance and texture, and promote healing. In particular, the topical composition of the present invention includes a concentrate derived from *Ecklonia maxima* (sea bamboo) providing a combination of bioactive components such as, for example, organic gels, vitamins, amino acids, enzymes and minerals, in combination with a dermatologically acceptable carrier.

In one aspect of the present invention, there is provided a topical composition comprising:

an amount of a concentrate derived from *Ecklonia maxima* (sea bamboo) effective for treating the skin, hair and/or nails; and a dermatologically acceptable carrier.

In another aspect of the present invention, there is provided a method of treating skin, hair and/or nails afflicted with a condition in need of treatment, comprising topically applying the topical composition described above to the skin, hair and/or nails afflicted with the condition.

DETAILED DESCRIPTION OF THE INVENTION

The present invention is directed to a topical composition formulated to treat skin, hair, and/or nails afflicted with a condition in need of treatment, and a method of using the same. The condition may be the result of aging and/or other damage in the skin, hair and nails due to environmental effects or stresses. The present invention is especially suitable for use in skin, hair and/or nails treatment applications. The present invention is specifically formulated to prevent or protect the skin, hair and/or nails against such conditions, improve visual appearance and texture, and promote healing. In particular, the topical composition of the present invention includes a concentrate derived from *Ecklonia maxima* (sea bamboo) providing a combination of bioactive components such as, for example, organic gels, vitamins, amino acids, enzymes and minerals, in combination with a dermatologically acceptable carrier.

The present invention alleviates conditions including, but not limited to, sun burns, post-waxing skin irritation, bug bites, fungal infections such as athlete's foot, itching and irritation due to poison ivy, oak, sumac, and nettles, rashes, razor burns, shingles, eczema, hyperpigmentation, scarring, psoriasis, dry and cracked skin, dry brittle hair and/or nails, dandruff, itchy scalp, and combinations thereof.

In one embodiment of the present invention, there is provided a topical composition comprising an amount of a concentrate derived from *Ecklonia maxima* (sea bamboo) effective for treating the skin, hair and/or nails, and a dermatologically acceptable carrier. The present topical composition is formulated to work at the cellular level to repair, promote skin, hair and/or nail health. In a further embodiment of the present invention, the amount of the *Ecklonia maxima* concentrate is in the range of from about 0.1 wt % to 99 wt % based on the total weight of the composition, preferably from about 10 wt % to 60 wt %, and more preferably at about 33.3 wt %.

*Ecklonia maxima* is a species of kelp native to the southern oceans, and is most typically found off the coast of the western tip of Africa. *Ecklonia maxima* is composed of a strong and rubbery cell structure which enables it to thrive in the violent wave action present on this coastal area. The strength of this marine kelp is due to the presence of high levels of organic gels within its tissue. In addition to organic gels, the kelp possesses significant amounts of vitamins, minerals, enzymes and amino acids. In the present invention, the concentrate of *Ecklonia maxima* contains high levels of cytoplasm and alginate, and is obtained from freshly harvested *Ecklonia* kelp via mechanical cell burst processing. This processing involves mechanical cell disruption, filtration and organic stabilization, and avoids chemical, irradiation, drying and other techniques that can diminish or destroy the actives in the concentrate. The *Ecklonia maxima* concentrate may contain trace amounts of hydrogen peroxide for extending preservation of the actives contained therein.

The actives of the present invention when applied to the skin, hair and/or nails forms a protective coating or membrane that provides skin benefits including, but not limited to, moisturization, hydration, re-hydration, nutritive delivery, skin texture enhancement, scar reduction or removal, wound healing promotion, hyperpigmentation relief, ultraviolet type A and type B protection, skin soothing relief from conditions causing irritation due especially to sun burn, waxing, bug bites, athlete's foot, poison ivy, oak, sumac and nettles, rash, razor burn, shingles, eczema, psoriasis, cracked skin, and the like; and that provides hair and/or nails benefits including, but not limited to, improved softness, improved manageability, improved luster and shine, improved thickness, improved moisturization and/or conditioning, improved color retention for color treated hair, hot iron damage relief, dandruff relief, itchy scalp relief, chemical treatment repair, damaged or dry nail cuticle repair, and the like.

The topical composition includes any suitable dermatologically acceptable carrier selected from aerosols, emulsion, liquid, foam, dispersions, creams, gels, pastes, ointments, sprays, serums, lotions, shampoos, bars, salves, and the like. In a preferred embodiment of the present invention, the topical composition is in the form of a serum. In a preferred embodiment of the present invention, the dermatologically acceptable carrier is deionized water. The dermatologically acceptable carrier may be present in an amount of from about 10 wt % to 99 wt % based on the total weight of the composition, and preferably from about 20 wt % to about 80 wt % and more preferably at about 64.34 wt %.

The topical composition may also include other optional ingredients including, but not limited to, pH adjusters, buffers, thickening agents, preservatives, colorants, pigments, fillers, opacifiers and perfumes.

The present invention further includes components especially useful in enhancing the shelf life of the actives present in the topical composition. In particular, the topical composition further includes a shelf life enhancer for maintaining the actives contained therein at optimal efficacy levels for an extended period of time as compared to compositions absent such enhancers. In a preferred embodiment of the present invention, the shelf life enhancer includes an antimicrobial effect.

In one embodiment of the present invention, the effective amount of the shelf life enhancer present in the topical composition is up to 40 wt % based on the total weight of the composition preferably from about 0.001 wt % to 30 wt % and more preferably from about 0.1 wt % to 20 wt %.

In a preferred embodiment of the present invention, the shelf life enhancer comprises an enzyme component and a substrate component. The enzyme component may be preferably selected from a peroxidase, an oxidase or combinations thereof, and the substrate component may be preferably selected from glucose, iodide or combinations thereof, which are catalytically compatible with at least one of the enzymes present in the topical composition.

In a further preferred embodiment of the present invention, the enzyme component is present in an amount of at least 0.001 wt % based on the total weight of the composition, preferably from about 0.025 wt % to 1 wt %, and more preferably at about 0.05 wt %, and the substrate component is present in an amount of at least 0.001 wt % based on the total weight of the composition, preferably from about 0.5 wt % to 10 wt %, and more preferably at about 1.0 wt %. In a further embodiment of the present invention, the weight ratio of the substrate component to enzyme component is at least 2:1, preferably from about 5:1 to 1001, and more preferably at about 20:1.

In a further embodiment of the invention, the present composition includes a buffer to maintain a pH value in the range of from about 4 to 6. This can be achieved by incorporating a buffer system such as, for example, citric acid and citrate. The buffer may be present in an amount of from about 1 wt % to 2 wt % based on the total weight of the composition. The addition of a buffer system minimizes downward drift of pH that may undesirably occur during storage and transport.

In a more preferred embodiment of the present invention, the topical composition includes an enzyme component comprising a peroxidase selected from lactoperoxidase, an oxidase selected from glucose oxidase, in combination with a substrate component comprising glucose.

In another embodiment of the present invention, there is provided a method of treating skin, hair and/or nails afflicted with a condition in need of treatment, comprising topically applying the topical composition of the present invention to the skin, hair and/or nails afflicted with the condition. The topical composition is applied in an effective amount sufficient to alleviate the condition for a given treatment regimen. The present topical composition may be topically applied to exposed areas of the body at least once, typically at least two times a day during use.

During application, a small quantity of the topical composition, for example from about 1 mL to 100 mL, may be applied to exposed areas of the body, from a suitable container or applicator, and if necessary, it is then spread over and/or rubbed into the skin, hair and/or nails using the fingers or hand or a suitable delivery apparatus. The application can be made through spraying.

EXAMPLES

Example 1

Chemical Analysis of *Ecklonia maxima* Kelp Concentrate

A chemical analysis of the *Ecklonia maxima* concentrate was made and the results of the analysis are provided in Tables 1-3 below.

TABLE 1

| COMPONENTS | | ADDITIVES | |
|---|---|---|---|
| Protein | 0.7 g/100 g | *Ecklonia maxima* seaweed (fresh material) | 33% |
| Amino acids | Very low | | |
| Carbohydrates | <1(LOQ)g/100 g | Water | 67% |
| Ashes | 0.6 g | | |
| Moisture | 99.0 g/100 g | | |
| Fat | 0.1 g/100 g | | |

TABLE 2

| GROWTH REGULATORS | | AMINO ACIDS | |
|---|---|---|---|
| AUXINS | 11 mg | Alanine | 0.58 mg |
| Indole-3-acetyl-L-aspartic acid (IAAsp) | | Valine | 0.04 mg |
| | | Glycine | 0.29 mg |
| Indole-3.acetylglycine (IAGly) | | Isoleucine | Not detected |
| | | Leucine | Not detected |
| Indole-3-acetyil-L-leucine (IALeu) | | Proline | 0.72 mg |
| | | Threonine | 0.31 mg |
| Indole-3-lactic acud (ILA) | | Serine | 0.11 mg |
| Indole-3-propionic acid (IPA) | | Methionine | 0.07 mg |
| Indoie-3-pyruvic acid (Ipia) | | Hydroxyproline | ≥trace amount |
| Indole-3-acetic add (1AA) | | Phenylalanine | Not detected |
| CYTOKININS | 0.03 mg | Aspartic Acid | Not detected |
| Trans-zeatin (tZ) | | Glutamic Add | Not detected |
| Cis-zeatin (cZ) | | Tyrosine | 1.01 mg |
| Trans-zeatin-O-glucoside (tZOG) | | Tryptophan | Not detected |
| | | Lysine | 0.04 mg |
| Cis-zeatin-o-glucoside (cZOG) | | Arginine | 0.15 mg |
| | | Histidine | Not detected |
| Trans-zeatin riboside-O-glucoside (tZROG) | | Cysteine | Not detected |
| Dihydrozeatin riboside (DHZR) | | | |
| Isopentenyladenine (iP) | | | |
| Benzyladenine (BA) | | | |
| Ortho-topolin (oT) | | | |
| Meta-topolin (mT) | | | |
| Ortho-topolin-o-glucoside (oTOG) | | | |
| Meta-topolin-o-glucoside (mTOG) | | | |

TABLE 3

| MACRO/MICRO NUTRIENTS | | PHYSICAL PROPERTIES | |
|---|---|---|---|
| Nitrogen (N) | 1618 mg/kg | State | Liquid |
| Phosphorus (P) | 2932 mg/kg | Viscosity | 3.9 cps |
| Potassium (K) | 6 mg/kg | Specific gravity | 1.007 (LTM 163) |
| Sulfur (S) | 1416 mg/kg | | |
| Calcium (Ca) | 3830 mg/kg | pH | 5.5 |
| Boron (B) | 8 mg/kg | Solubility | Soluble in Water |
| Copper (Cu) | 307 mg/kg | | |
| Iron (Fe) | 628 mg/kg | Boiling point | 95° C. |
| Magnesium (Mg) | 3930 mg/kg | Receding surface tension (dynes/cm) | 63.6 |
| Manganese (Mn) | 42 mg/kg | | |
| Zinc (Zn) | 206 mg/kg | VITAMINS | |
| Lead (Pb) | 1.32 mg/kg | Vitamin A | None detected |
| Cadmium (Cd) | 0.24 mg/kg | Vitamin E | None detected |
| Chromium (Cr) | 2 16 mg/kg | Vitamin C | 0.6 mg/100 g |
| Nickel (Ni) | 3.12 mg/kg | | |
| Tin (Sn) | 0.21 mg/kg | | |
| Sodium (Na) | 12 mg/kg | | |
| Chlorine (Cl) | 11.3 mg/kg | | |

Example 2

Topical Composition of the Present Invention Formulated as a Spray Serum

The components of a topical composition of the present invention formulated as a spray serum are listed in Table 4 below.

TABLE 4

| Component | Amount (Wt %) |
|---|---|
| *Ecklonia maxima* kelp concentrate | 33.3 |
| Substrate Solution (INCI name, Glucose) | 1.00 |
| Enzyme Solution (INCI name, Lactosperoxidase/Glucose oxidase) | 0.05 |
| Citric acid | 0.35 |
| Sodium citrate | 0.96 |
| Deionzed water | 64.34 |
| Total | 100 |

The spray serum formulation in the form of a water-like emulsion is characterized as having a pH value of from about 4.2 to 6.5 with a water-like viscosity suitable for application as a spray.

Example 3

Formulation Process for Preparing the Topical Composition of Example 2

The topical composition of Example 2 was prepared in the amounts listed in Table 4 in a suitable mixing vessel equipped with a propeller agitator at about room temperature. The *Ecklonia maxima* kelp concentrate was filtered through a sieve-like material (e.g., cheesecloth) into the vessel. The propeller agitator was set at moderate mixing speed. Purified water deionized water was added to the vessel while mixing. Thereafter, citric acid was then added to the mixture and mixed until completely dissolved.

Sodium citrate USP anhydrous was then slowly added into the mixture to achieve a pH in the range of from about 4.9 to 5.1. It is noted that if the pH value of the mixture goes above 5.1, add citric acid in small amounts to adjust the pH accordingly. Correspondingly, if the pH value of the mixture goes below 4.9, add sodium citrate in small amounts to adjust the pH accordingly.

Once the desired pH was achieved, the glucose component was added to the mixture and mixed for about 15 minutes. After 15 minutes of mixing, the Lactoperoxidase/Glucose oxidase component was added to the mixture and mixed for about 30 minutes until uniformity was achieved. The final pH was then measured and checked to ensure proper pH range parameters.

The foregoing discussion discloses and describes merely exemplary embodiments of the present invention. One spilled in the art will readily recognize from such discussion, and from the accompanying drawings and claims, that various changes, modifications and variations can be made therein without departing from the spirit and scope of the invention as defined in the following claims.

What is claimed is:

1. A topical composition comprising:
   an amount of 0.1 wt % to 99 wt % based on the total weight of said composition of a concentrate derived from *Ecklonia maxima* effective for treating the skin, hair and/or nails;
   an amount of 0.001 wt % to 40 wt % based on the total weight of said composition of a shelf life enhancer;
   about 1 wt % to 2 wt % based on the total weight of said composition of a dermatologically acceptable buffer suitable to buffer the composition to a pH in the range of 4 to 6 and a dermatologically acceptable carrier;
   said concentrate obtained in the absence of chemical techniques, irradiation or drying;
   said shelf life enhancer consisting essentially of an enzyme component and a substrate component;
   said enzyme component comprising at least a peroxidase and at least an oxidase; and
   said substrate component comprising at least glucose and at least iodide.

2. The topical composition of claim 1 wherein the amount of the concentrate is in the range of from about 10 wt % to 60 wt %.

3. The topical composition of claim 1 wherein the amount of the concentrate is about 33.3 wt %.

4. The topical composition of claim 1 wherein the composition is formulated as a serum.

5. The topical composition of claim 1 wherein the effective amount of the shelf life enhancer is in the range of from about 0.001 wt % to 30 wt %.

6. The topical composition of claim 1 wherein the effective amount of the shelf life enhancer is in the range of from about 0.1 wt % to 20 wt %.

7. The topical composition of claim 1 wherein the peroxidase is lactoperoxidase.

8. The topical composition of claim 1 wherein the oxidase is glucose oxidase.

9. The topical composition of claim 1 wherein the enzyme component is present in an amount of at least 0.001 wt % based on the total weight of the composition.

10. The topical composition of claim 1 wherein the amount of the enzyme component is in the range of from about 0.025 wt % to 1 wt %.

11. The topical composition of claim 1 wherein the amount of the enzyme component is about 0.05 wt %.

12. The topical composition of claim 1 wherein the substrate component is present in an amount of at least 0.001 wt % based on the total weight of the composition.

13. The topical composition of claim 1 wherein the amount of substrate component is in the range of from about 0.5 wt % to 10 wt %.

14. The topical composition of claim 1 wherein the amount of substrate component is about 1.0 wt %.

15. The composition of claim 1 wherein said buffer is a citrate buffer.

16. A topical composition comprising:
an amount of 0.1 wt % to 99 wt % based on the total weight of said composition of a concentrate derived from *Ecklonia maxima* effective for treating the skin, hair and/or nails;
an amount of 0.001 wt % to 40 wt % based on the total weight of said composition of a shelf life enhancer;
about 1 wt % to 2 wt % based on the total weight of said composition of a dermatologically acceptable buffer suitable to buffer the composition to a pH in the range of 4 to 6 and
a dermatologically acceptable carrier;
said concentrate obtained in the absence of chemical techniques, irradiation, or drying;
said shelf life enhancer consisting essentially of an enzyme component and a substrate component;
said enzyme component comprising at least a lactoperoxidase and at least a glucose oxidase; and
said substrate component comprising at least glucose and iodide.

17. The composition of claim 16 wherein said buffer is a citrate buffer.

18. The topical composition of claim 16 wherein the weight ratio of substrate component to enzyme component is at least 2:1.

19. The topical composition of claim 16 wherein the weight ratio of substrate component to enzyme component is in the range of from about from about 5:1 to 100:1.

20. The topical composition of claim 16 wherein the weight ratio of substrate component to enzyme component is about 20:1.

21. A method of treating skin, hair and/or nails in need of treatment, comprising topically applying the topical composition of claim 1 to the skin, hair and/or nails.

* * * * *